US009019099B2

(12) United States Patent
Fox et al.

(10) Patent No.: US 9,019,099 B2
(45) Date of Patent: Apr. 28, 2015

(54) SYSTEMS AND METHODS FOR PATIENT MONITORING

(71) Applicant: Covidien LP, Mansfield, MA (US)

(72) Inventors: David Fox, Longmont, CO (US); Robert T. Boyer, Longmont, CO (US); William A. Jordan, Westminster, CO (US)

(73) Assignee: Covidien LP, Mansfield, MA (US)

( * ) Notice: Subject to any disclaimer, the term of this patent is extended or adjusted under 35 U.S.C. 154(b) by 158 days.

(21) Appl. No.: 13/674,662

(22) Filed: Nov. 12, 2012

(65) Prior Publication Data

US 2014/0132413 A1 May 15, 2014

(51) Int. Cl.
| | | |
|---|---|---|
| *G08B 1/08* | (2006.01) | |
| *G06F 19/00* | (2011.01) | |
| *A61B 5/0205* | (2006.01) | |
| *A61B 5/11* | (2006.01) | |
| *A61B 5/00* | (2006.01) | |
| *A61B 5/021* | (2006.01) | |
| *A61B 5/08* | (2006.01) | |
| *A61B 5/145* | (2006.01) | |

(52) U.S. Cl.
CPC ............. *G06F 19/327* (2013.01); *A61B 5/7207* (2013.01); *A61B 5/0022* (2013.01); *A61B 5/02055* (2013.01); *A61B 5/021* (2013.01); *A61B 5/0816* (2013.01); *A61B 5/1128* (2013.01); *A61B 5/14542* (2013.01); *Y10S 128/903* (2013.01)

(58) Field of Classification Search
CPC ........ G08B 1/08; G08B 21/02; A61B 5/0002; A61B 5/0022; A61B 5/1128; A61B 5/7207; G06F 19/327; G06F 19/3418
USPC ................. 340/573.1, 539.1, 539.11, 539.12, 340/286.07, 691.6; 600/300, 301; 128/903, 128/904, 920, 921; 348/14.01, 14.03, 348/14.08, 77, 143
See application file for complete search history.

(56) References Cited

U.S. PATENT DOCUMENTS

| | | | |
|---|---|---|---|
| 5,441,047 A | 8/1995 | David et al. | |
| 6,057,758 A * | 5/2000 | Dempsey et al. | ........ 340/539.12 |
| 6,871,211 B2 * | 3/2005 | Labounty et al. | ............. 709/203 |
| 7,038,588 B2 | 5/2006 | Boone et al. | |
| 7,965,309 B2 | 6/2011 | Mattila et al. | |
| 8,120,471 B2 * | 2/2012 | Collins et al. | ............ 340/286.07 |
| 2003/0107487 A1 * | 6/2003 | Korman et al. | ............ 340/573.1 |
| 2005/0206518 A1 * | 9/2005 | Welch et al. | ............ 340/539.12 |
| 2012/0075464 A1 | 3/2012 | Derenne et al. | |
| 2012/0140068 A1 | 6/2012 | Monroe et al. | |

* cited by examiner

*Primary Examiner* — Hung T Nguyen
(74) *Attorney, Agent, or Firm* — Carter DeLuca Farrell & Schmidt LLP (57) ABSTRACT

A method of receiving data indicative of at least one physiological parameter of a patient, receiving image data of the patient, determining that a value of the at least one physiological parameters signifies an alarm condition in the patient, generating an alarm data set including image or audio data of the patient and the value of at least one physiological parameter, and transmitting a notification of the alarm condition including the alarm data set to a clinician.

20 Claims, 8 Drawing Sheets

SYSTEMS AND METHODS FOR PATIENT MONITORING

TECHNICAL FIELD

The present disclosure relates generally to patient monitoring, and more particularly to a system, method, and software for patient monitoring.

BACKGROUND

When monitoring a patient, a medical device may collect and display information about that patient. The medical device may collect information through one or more of a variety of ways, such as a patient interface that measures a physiological condition, or a user interface that collects information input by a user. The collected information is often considered in view of various thresholds, and when the collected information falls outside those thresholds, an alarm may sound signifying a potential issue of the patient requiring the attention of one or more medical professionals.

SUMMARY

Aspects of the present disclosure are directed to a system, method, and computer readable recording medium capable of performing the steps of receiving data indicative one or more physiological parameter of a patient, receiving image data of the patient, determining that a value of the physiological parameter(s) signifies an alarm condition in the patient, generating an alarm data set including image data of the patient and the value of the physiological parameter(s), and transmitting a notification of the alarm condition including the alarm data set to a clinician.

By incorporating the image data with data indicating an alarming condition a clinician is better able to contextualize the incidence of an alarm, make better decisions regarding that alarm, and make better diagnoses for a patient.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

The present disclosure incorporates the use of video and audio patient data along with the other patient data generated by the medical devices 102. By incorporating the video data, and making it available for viewing along with the alarm data, a clinician can make more informed decisions regarding the patient than would be possible if the clinician were relying just on the data from the medical devices alone. Moreover, by coordinating the video data and the alarm data, and considering the combination over a historical period a tool is created allowing for further analysis of a patient's condition and may result in the diagnosis of a condition to which the patient had not yet developed other appreciable symptoms.

As an example, if a patient is connected to a pulse oximetry meter, such devices are known to be particularly sensitive to movement of a patient. Thus, if connected to a patient that is rolling over in their bed, the detected saturated oxygen levels of a patient may momentarily change and result in an alarming condition. The clinician receiving the notice of alarm at, for example, a nurse's station is not likely to be aware that the patient has rolled over in their bed and must simply proceed to the patient's room and silence the alarm. But outwardly there is no reason that the clinician might be able to discern as to why the alarming condition occurred in the first place, particularly if by the time the clinician arrives at the patient the oxygen levels are in a non-alarm condition and the patient is again sleeping. And while this might be considered a benign occurrence where the patient rolled over in bed, the same outward scenario could also occur where a patient has a short duration seizure. In such a situation, the clinician would have no way of knowing that the seizure had taken place and that there may be some other undiagnosed condition that requires treatment.

However, according to the present disclosure the use of the video data allows the clinician to not only receive the notification of the alarm as a result of the low saturated oxygen of a patient, but also to consider the video data associated with that alarm condition. Accordingly, the clinician can determine that the patient was just rolling over and that the alarm is merely an indicator of such due to the pulse-oxymetry device's sensitivity to movement. Alternatively, by viewing the video data associated with the alarm, the clinician can view the patient suffering a seizure and, therefore, alert relevant personnel to this far more serious condition. Accordingly, the video data allows the clinician to put any alarm in context of what the patient is doing at the time of the alarm.

Another scenario where video data and movement of the patient can be important to the analysis of and alarming condition is blood pressure monitoring. A patient whose blood pressure suddenly drops could be in serious danger if that patient is not moving at the time of the blood pressure drop. Indeed such a drop could be the result of internal bleeding, heart failure, or a number of other conditions. In such situations, the patient is unlikely to be moving. By contrast, a patient who stands up from their bed in order to take a walk or visit the lavatory may experience a short-term drop in blood pressure such that an alarm might sound. In this scenario, a nurse viewing the movement of the patient would immediately understand that the condition is a result of the patient's standing up, and that a patient standing is a common reason for blood pressure to drop. A non-moving patient, however, suffering a drop in blood pressure may be experiencing a server condition change requiring significant and immediate medical intervention.

Further, according to certain aspects of the present disclosure, because the patient and alarm data are stored in memory on, for example, a server, they are available for consideration by a clinician at a later date. For example, in the situation where the patient is frequently triggering the low blood pressure alarm due to frequently leaving the bed to go to the lavatory, a clinician noting this repeated movement in a patient being treated for an unrelated condition might be able to assess that the frequent need to urinate is possibly an indicator of another condition, e.g., an enlarged prostate, and schedule the patient for the relevant screening.

Still further, the stored historical data, including the video and audible data can be reviewed for auditing purposes to assess the quality of care a patient received. This may be desirable in situations where injury is alleged due to medical malpractice, and either a hospital or insurer is seeking to demonstrate that there was no lapse in care by the timely assessment of all alarming conditions. Similarly, the alarm and video data may be useful in conducting audits of medical professionals, a hospital's ability to conduct a specific type of treatment regimen, or other analysis of the patient, hospital, staff, or condition. As will be appreciated, certain embodiments of the present disclosure relate to collecting the patient data including the video data and presenting the data to clinicians remote from the patient for analysis.

Figure 1:
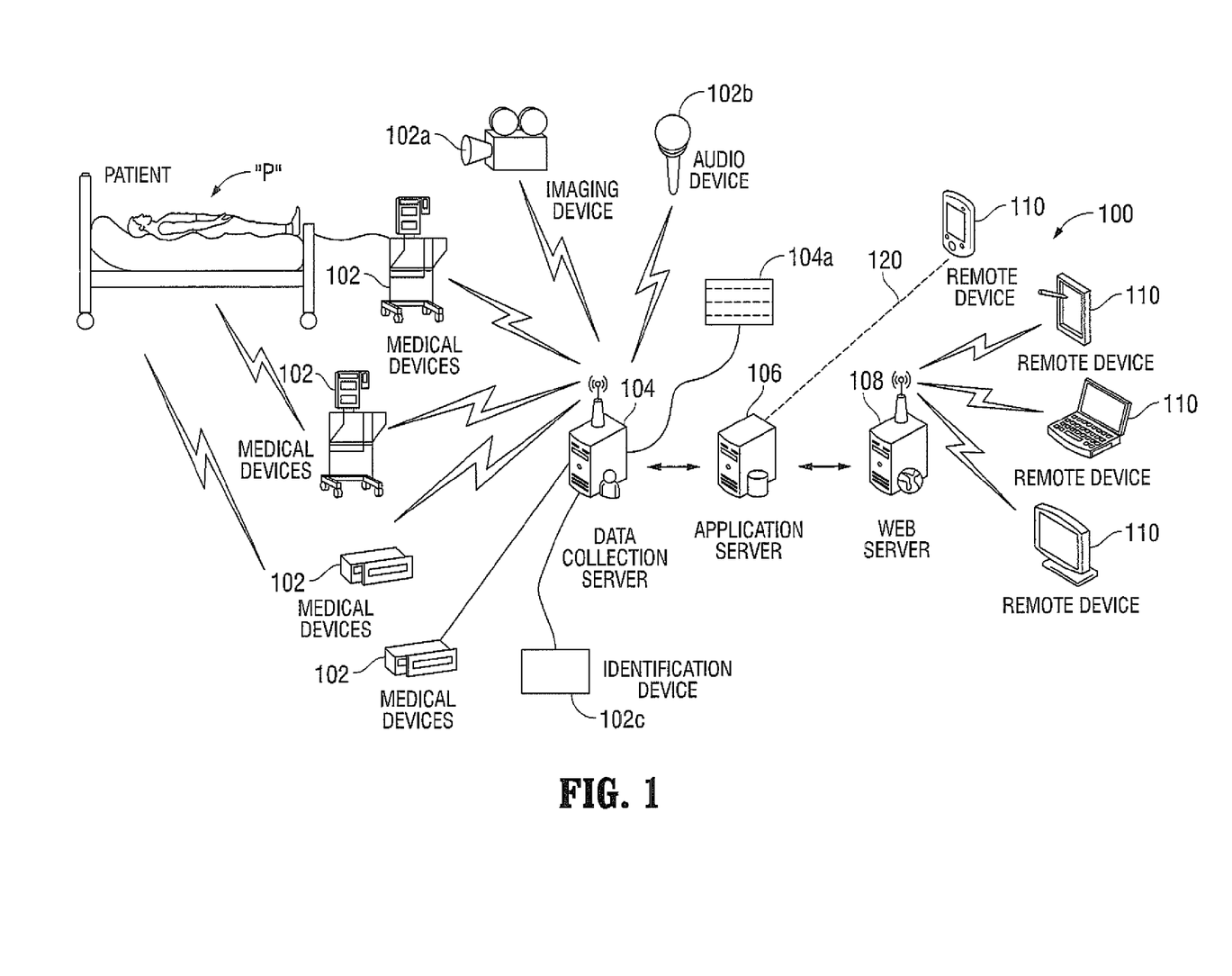
FIG. 1 illustrates an example system for patient monitoring, according to certain embodiments of the present disclosure.

FIG. 1 illustrates an example system 100 for patient monitoring, according to certain embodiments of the present disclosure. System 100 includes one or more medical devices 102, an imaging device 102a, an audio device 102b, an identification device 102c, a data collection server 104, an application server 106, a web server 108, and one or more remote devices 110. Although this particular implementation of system 100 is illustrated and primarily described, the present disclosure contemplates any suitable medical network implementation of system 100 according to particular needs of the institution or facility.

Medical devices 102, imaging device 102a, and/or audio device 102b generate data relating to, among other things, the identity of the patient "P," physiological parameters of the patient, and image and audio data of the patient. System 100 collects the data and using various protocols and software is capable of transforming the data such that it can be readily accessed and analyzed via one or more graphic user interfaces (GUI), including some that might be viewed on a remote devices 110. Further, system 100 may be configured to receive identification information regarding the particular medical devices 102 via the imaging device 102a, or another identifying device 102c, to associate the particular medical device 102 with the particular patient "P" being monitored.

Each medical device 102 may be connected to data collection server 104, which stores the patient data in a database 104a. Database 104a may be configured, among other things, to store data relating to, instances of alarming conditions associated with the patient data as well as medical device setpoints, image and audio data of the patient, and clinician activities. Application server 106 may retrieve the patient data from the database 104a and processes the patient data. A web server 108 may be employed to publish the patient data processed by the application server 106, such that it may be viewed on a GUI on a remote device 110, thereby enabling clinicians using the remote device 110 to view the patient data from remote locations. In this context, remote can mean any location not immediately adjacent the patient and may include a hospital floor nurse's station, a central alarm monitoring station for a hospital, and smartphones or tablets operated by a clinician, e.g., an on-call physician far removed from the patient.

As noted above, system 100 may include one or more medical devices 102. In certain embodiments, the medical devices 102 may generate and store patient data, whether generated by monitoring of the patient or input into the medical device by a clinician. Patient data may include any patient identifiers, medical history, clinician notes, alarm thresholds, alarm events, device settings, measurements of values indicating physiological conditions such as oxygen saturation levels, pulse rates, heart rates, other vital signs, and any other data input to or output from medical devices 102. Medical devices 102 may be any devices that are used for monitoring, tracking or treating patients. For example, medical devices 102 may include a ventilator connected to a patient to deliver respiration therapy, a pulse oximeter that monitors the oxygen saturation of a patient's blood, a device for tracking a patient within a hospital with or without monitoring a physiological condition, as well as other medical devices known to those of skill in the art. Medical devices 102 may include a component for identifying the particular medical device 102, including, but not limited to, radio frequency identification chips and unique bar codes.

System 100 may further include one or more imaging devices 102a, which generates data that may be associated with patient data as will be described in greater detail below. Image data may include a single image, multiple images, and/or video of a patient for storage in the database 104a. The imaging device 102a may be capable of pan, tilt, and zoom movements and may include any suitable device for capturing an image, series of images, and/or video. The imaging device 102a may be driven in its pan, tilt and zoom movements by input from a user, as is known in the art, either from a remote station on the system 100 network, or from a remote device 110. Additionally, or alternatively, the imaging device 102a may include auto-tracking abilities for panning, tilting, and zooming based on movement of the subject, e.g. the patient. In this manner, the imaging device 102a can ensure to the greatest extent possible that the patient remains in view and greater detailed data regarding the movements of the subject can be gathered.

Imaging device 102 may include, without limitation, one or more digital charge-coupled devices (CCD), complementary metal-oxide-semiconductor (CMOS) active pixel sensor, or combinations/hybrids of the two, whether for capturing visible or infrared spectrum light, as well as other image sensors known to those of skill in the art.

Imaging device 102a may be further configured to capture identification data of the patient "P" and/or the medical devices 102 being used to monitor patient "P," and deliver the identification data to the data collection server 104 for further processing to associate the particular medical devices 102 with the particular patient "P" being monitored by the medical device 102. For example, and without limitation, the medical devices 102 may include bar codes which may be scanned by imaging device 102a, and may include facial recognition capabilities to identify the patient "P." Similarly, a bar code attached to a medical device 102 may be read by the imaging device 102a. The system 100 may then associate the specific medical devices 102 with the particular patient "P" being monitored. If the medical devices 102 are ever changed, or used for a different patient, or if new medical devices 102 are used for the same patient "P," then the imaging device 102a may capture a new image of the medical device's 102 new bar code such that the data collection server 104 can update the medical device 102 associated with the patient "P."

System 100 may include one or more audio devices 102b to collect audio data related to the patient in a manner similar to that described above with respect to image data. This data may be similarly stored in the data collection server 104 and reviewed by, for example, a remote device 110.

System 100 may also include one or more identification devices 102c. In certain embodiments, identification device 102c may be incorporated into imaging device 102a. Additionally, or alternatively, identification device 102c may include a radio frequency identification (RFD) reader, and/or a bar code scanner/reader, used for identifying the medical devices 102 and correlating particular devices, and the data they generate with a particular patient.

As noted above, in addition to performing a medical function, medical devices 102, imaging device 102a, and/or audio device 102b may generate patient data. For example, the ventilator may generate data indicating the average volume of air expelled in each breath, or the respiratory rate of a patient. This patient data may be stored locally on the medical device 102 or output to a data collection server 104, or both. The ventilator may also store or output to the data collection server 104 data identifying the settings of the ventilator and whether any alarms have been triggered. The patient data from the medical device 102, imaging device 102a, and/or audio device 102b may be constantly streamed, periodically posted to the data collection server 104, or the data collection server 104 may periodically poll the medical device 102. Further, other protocols may be employed based on alarming conditions, such that the data collection server 104 receives important data in a timely manner, regardless of any set period for collection of the patient data.

Medical devices 102, imaging device 102a, and/or audio device 102b may be communicatively coupled to data collection server 104 via a network such as a LAN, WAN, or WiLAN employing one or more of well known network communication protocols. In certain embodiments, medical devices 102, imaging device 102a, and/or audio device 102b may also be communicatively coupled to the application server 106, web server 108, and remote devices 110.

Data collection server 104 may include one or more electronic computing devices operable to receive, transmit, process, and store data associated with system 100. In addition, data collection server 104 may use any suitable operating system, as would be understood by those of skill in the art. Although a single data collection server 104 is illustrated, the present disclosure contemplates system 100 including any suitable number of data collection servers 104. Moreover, although referred to as a data collection server, the present disclosure contemplates data collection server 104 comprising any suitable type of processing device or devices.

Data collection server 104 may map received patient data to match internal fields in a database 104a according to certain embodiments.

The stored patient data in the database 104a, or otherwise on the data collection server 104, may be accessed by application server 106. Application server 106 may include one or more electronic computing devices operable to receive, transmit, process, and store data associated with system 100. In addition, application server 106 may use any suitable operating system. Although a single application server 106 is illustrated, the present disclosure contemplates system 100 including any suitable number of application servers 106. Moreover, although referred to as an application server, the present disclosure contemplates application server 106 comprising any suitable type of processing device or devices.

According to one embodiment, application server 106 runs one or more applications through which the data collected by the data collection server 104 can be processed and made presentable to a user. In one example, the application server 106 includes a data service that runs on a conventional web services platform for transmitting data to web server 108. Application server 106 may include a database server in certain embodiments. According to one embodiment, application server 106 may include a logical system that may execute an algorithm, such as a clinical application using patient data. For example, application server 106 may process the patient data and the processed data may then be transmitted to web server 108. Application server 106 may maintain an activity log that logs data requests from remote devices 110 to track certain activities performed at remote devices 110. Therefore, if a clinician selects a particular patient in order to view ventilator data specific to that patient, that selection may trigger a data request that is logged by application server 106.

When processing patient data in response to a selection made on a remote device 110, the application server 106 may compare the current settings of a medical device 102, as indicated in the application database 104a, to prior settings. If any changes are detected, application server 106 may flag those changes for presentation to users on remote devices 110 as an alarm. The application server 106 may perform any number of application specific activities in response to the patient data and requests made from remote devices 110. For example, application server 106 may create data causing the display on remote devices 110 to change color in response to receiving additional patient data. The additional patient data may include new data, for example, data associated with an additional machine or patient being monitored. The additional patient data may further include changes in patient data, such as a change in a temperature of a patient. Application server 106 may create additional display features that cause a pop-up window to appear on the remote device 110. The pop-up window may list all of the changed/additional data and provide a button through which a clinician may indicate that that the changed/additional data has been viewed. If that button is activated, the mobile device 110 may transmit a message to application server 106 by way of web server 108. In certain embodiments, application server 106 may transmit data directly to remote devices 110.

System 100 may include one or more web servers 108. Web server 108 may include one or more electronic computing devices operable to receive, transmit, process, and store data associated with system 100, and may use any suitable operating system. Moreover, although referred to as a web server, the present disclosure contemplates web server 108 comprising any suitable type of processing device or devices.

According to one embodiment, web server 108 creates a data service that publishes a conventional web services platform, which receives data from application server 106, transmits data to remote devices 110, and receives data from remote devices 110 for distribution back to the application server 106 and the data storage server 104. For example, web server 108 may receive data from application server 106 and transmit data, upon request to remote devices 110.

System 100 may include one or more remote devices 110. Remote devices 110 may be any device that provides output to, and can receive input from, a user, such as a clinician. Each remote device 110 may include one or more computer systems at one or more locations. In certain embodiments, output at remote devices 110 may include vibrations, display views including pop-up messages, sound, or any combination desired. In some embodiments, remote devices 110 may connect directly to application server 106 through a direct socket connection, as indicated by reference number 120 in FIG. 1. In such instances, the remote device 110 is able to connect directly to the applications running on the application server 106, and does not require the use of the web server 108. Such a configuration may be useful for accessing the patient data at locations within a hospital or medical facility such as at a nurse's monitoring station or a general hospital patient monitoring station. Direct connection to the application server 106 may, in some instances, provide greater access to the patient data as well as greater options for refinement or distillation of the data, as would be understood by those of skill in the art, when compared to the data made available via the web server 108 for review by remote devices. Simply put, by connecting directly to the application server 106, a user is able to harness the full functionality of the data processing applications running on the application server 106, whereas full functionality may not be possible or desirable as the patient data is processed for publication at the web server 108 and accessed by remote devices 110 over, for example, the internet.

Each remote device 110 may include any appropriate input components (such as a keypad, touch screen, mouse, or other device that can accept input), output devices, mass storage media, or other suitable components for receiving, processing, storing, and communicating data.

According to one embodiment, remote devices 110 display one or more web pages hosted by application server 106 and/or web server 108 and display data relating to a patient and the medical devices 102 to which the patient is connected. The remote device 110 may also receive data from the imaging devices 102a and the audio devices 102b. For example, a clinician may activate a browser on remote device 110 and navigate to a web page hosted by web server 108. The browser may render the web page, which includes data processed by application server 106. The web page may provide a summary of all medical devices 102, imaging device 102a, and/or audio device 102b under a clinician's responsibility. In addition, the web page may enable a detailed view that displays specific device data, therapy parameter data, and alarm status data.

Although FIG. 1 depicts separate devices for data collection server 104, application server 106, and web server 108, it will be readily apparent that the functions of these devices may be combined into just two servers or even a single device that receives patient data from medical devices 102, imaging device 102a, and/or audio device 102b, and processes the patient data such that it can be displayed on one or more remote devices 110. It will also be understood that the functions may be allocated differently than shown, with application server 106 additionally performing the functions of web server 108 or the functions of data collection server 104.

In summary, FIG. 1 depicts a system 100 enabling the generation and collection of patient data, the storing of patient data, the processing of patient data, the publishing of patient data to one or more web pages, and the accessing of patient data by a clinician or other medical professional on a remote device for real-time notification and analysis as well as historical analysis.

Figure 2:
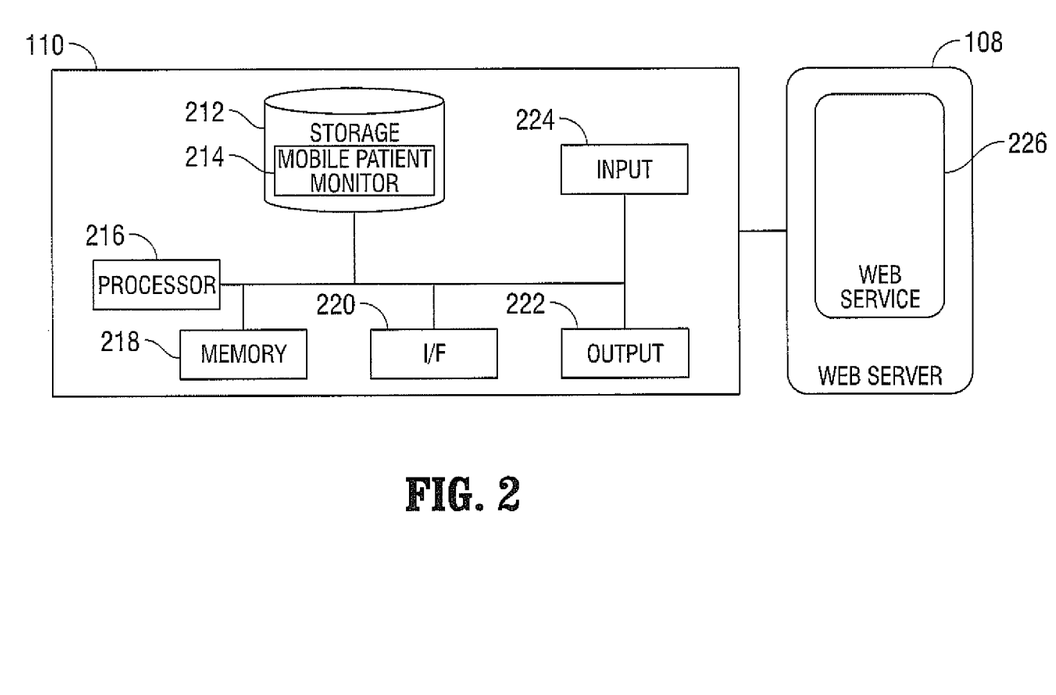
FIG. 2 is a schematic illustration of an example remote device of the system for patient monitoring in FIG. 1, according to certain embodiments of the present disclosure.
Figure 3:
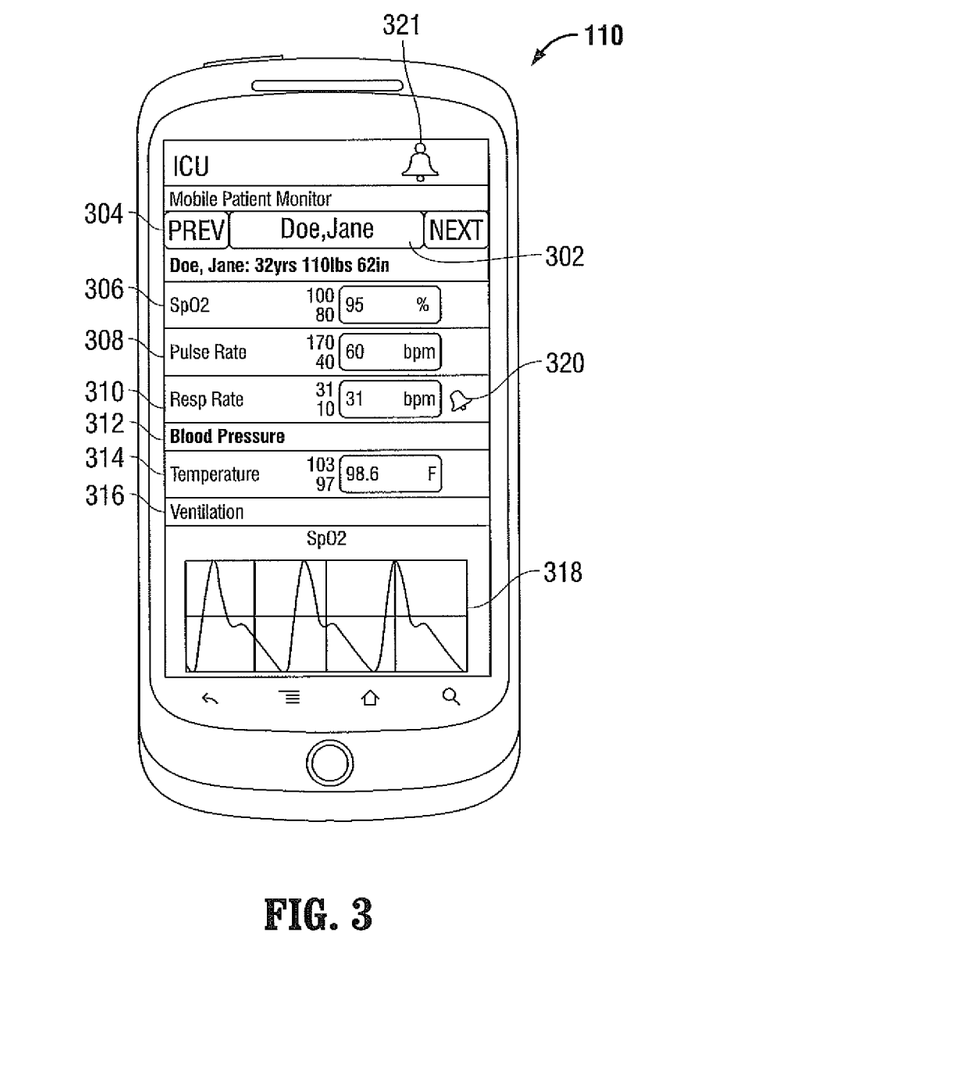
FIG. 3 is a front view of an example remote device of the system for patient monitoring in FIG. 1 displaying a first screen with a first set of parameters, according to certain embodiments of the present disclosure.

FIG. 2 illustrates an example remote device 110 of the system 100 for patient monitoring in FIG. 1, according to certain embodiments of the present disclosure. In FIG. 3, remote device 110 is shown as a mobile telephone. Remote device 110 is communicatively coupled with a web server 108 having a web service 226 capability. Remote device 110 may include in certain embodiments a storage device 212 and a mobile patient monitor 214 stored on the storage device 212. The remote device 110 further includes a processor 216, a memory 218, a communication interface (I/F) 220, an output device 222, and an input device 224, which are described in further detail below. Although this particular implementation of remote device 110 is illustrated and primarily described, the present disclosure contemplates any suitable implementation of remote device 110 according to particular needs.

Storage device 212 may include any suitable device operable for storing data and instructions. Storage device 212 may include, for example, Random Access Memory (RAM) or Read Only Memory (ROM), EEPROM, a magnetic disk, flash memory, optical disk, or other suitable data storage device.

Mobile patient monitor 214 may include any suitable logic embodied in computer-readable media, that when executed is operable to enable a user to communicate with web service 226 on web server 108 to view and manipulate data, including patient data. For example, mobile patient monitor 214 may include logic for receiving data from input device 224 and translating the data into a message to be sent to web service 226 on web server 108, in turn enabling a user to activate a browser and navigate a web page generated by web service 226 on web server 108 to view patient data. The browser may provide, as part of the patient data, a summary of all medical devices 102, imaging device 102a, and/or audio device 102b associated with patients under a caregiver's responsibility, or a detailed view that displays specific medical device 102, imaging device 102a, and/or audio device 102b configuration data, therapy data, and alarm status data. Mobile patient monitor 214 may be configured to cause remote device 110 to periodically request the most recent webpage data from web service 226 on web server 108.

When mobile patient monitor 214 requests patient data (for example, by clicking a navigation link embedded in a web page display), the browser transmits the request to web service 226. In embodiments with a browser, web service 226 may extract the request and transmit a copy of the requested data in a format suitable for display by the browser, as well as any required formatting code, such as HTML code, and/or computational code, such as Javascript, for example. In certain embodiments, formatting code may not be present, such as, for example, in embodiments with a native application at the remote device. Examples of the patient monitor 214 may include a thick client such as a native application that runs of the remote device 110 and which receives data from the web server 108 and conducts its own processing and data manipulation. Alternatively, the patient monitor 214 may be a thin client interface enabling display of data received from the web server 108, and all processing and data manipulation occurs at the application server 106 or the web server 108 and available via a browser such as Mozilla (Firefox), Internet Explorer, Google Chrome, Safari or any other current or future browsers.

Processor 216 may include any suitable device operable to execute instructions and manipulate data to perform operations for mobile patient monitor 214. Processor 216 may include, for example, any type of central processing unit (CPU).

Memory 218 may include any computer memory (for example, Random Access Memory (RAM) or Read Only Memory (ROM)), mass storage media (for example, a hard disk), removable storage media (for example, a Compact Disk (CD), a Digital Video Disk (DVD), or USB Flash Drive), database and/or network storage (for example, a server). Memory 218 may comprise any other computer-readable tangible medium, or a combination of any of the preceding.

I/F 220 may include any suitable device operable to receive input for mobile patient monitor 214, send output from mobile patient monitor 214, perform suitable processing of the input or output or both, communicate to other devices, or any combination of the preceding. I/F 220 may include appropriate hardware (for example, a modem, network interface card, etc.) and software, including protocol conversion and data processing capabilities, to communicate through a LAN, WAN, or other communication system that allows mobile patient monitor 214 to communicate to other devices. I/F 220 may include one or more ports, conversion software, or a combination of any of the preceding.

Output device 222 may include any suitable device operable for displaying information to a user. Output device 222 may include, for example, a touch screen, a video display, a printer, a plotter, or other suitable output device.

Input device 224 may include any suitable device operable to input, select, and/or manipulate various data and information. Input device 224 may include, for example, a touch screen, a keyboard, mouse, graphics tablet, joystick, light pen, microphone, scanner, or other suitable input device.

Modifications, additions, or omissions may be made to remote device 110 without departing from the scope of the disclosure. The components of remote device 110 may be integrated or separated. Moreover, the operations of remote device 110 may be performed by more, fewer, or other components. For example, although mobile patient monitor 214 is displayed as part of storage device 212, mobile patient monitor 214 may be stored in any suitable location and the operations of mobile patient monitor 214 may be performed by more than one component. Additionally, operations of remote device 110 may be performed using any suitable logic. As used in this document, "each" refers to each member of a set or each member of a subset of a set.

One issue associated with hospital monitoring systems like system 100 is the occurrence of alarm fatigue. This can occur when a patient or multiple patients have reoccurring alarms which, though indicating a concern for their condition often, are not themselves threatening to the patient. As understood by medical professionals, when an alarm for a patient repeatedly sounds, despite any significant change in the patient's condition over time the medical professional begins to ignore the alarm as nothing more than an indication that the condition is continuing. This is particularly challenging in environments where nurses and other medical professionals are monitoring an entire floor of patients and the alarms are relatively continuous. It becomes very challenging to stay focused, treat the alarms with the necessary care, and also to allocate their resources appropriately or to triage multiple alarms coming in rapid succession from multiple patients.

Figure 5:
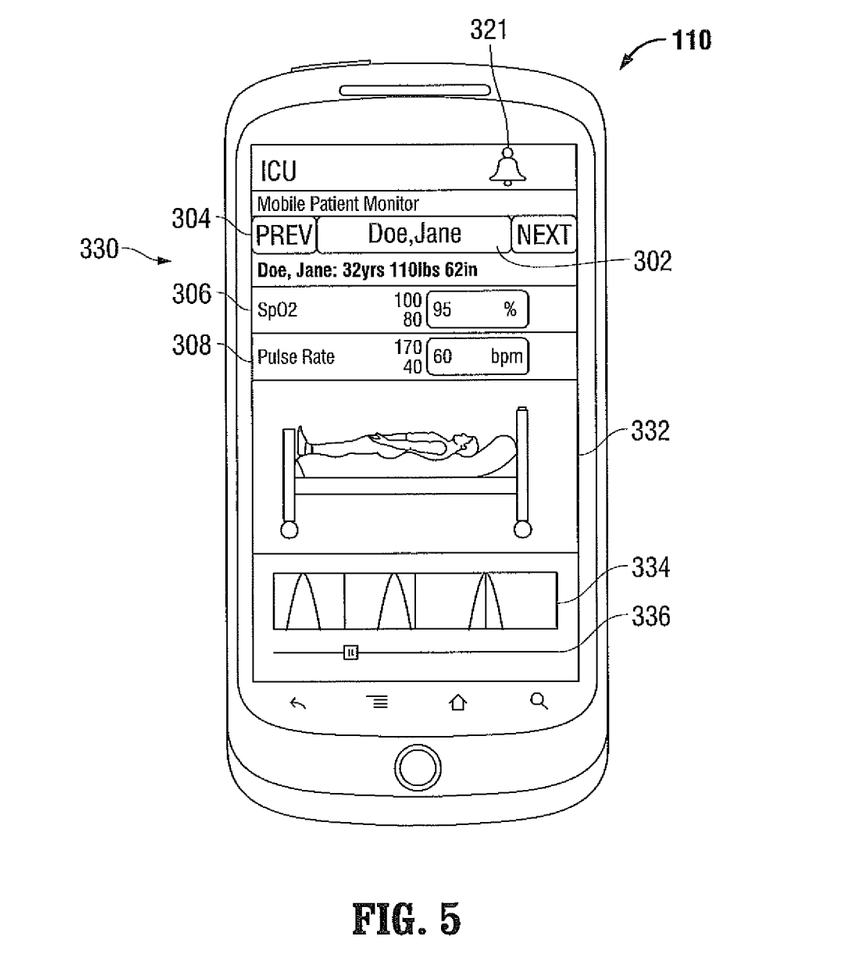
FIG. 5 is a front view of an example remote device of the system for patient monitoring in FIG. 1 displaying a second screen, according to certain embodiments of the present disclosure.

FIG. 3 illustrates an example remote device 110 of the system 100 for patient monitoring in FIG. 1, according to certain embodiments of the present disclosure. In FIG. 3, remote device 110 is shown displaying a first set of patient data. In FIG. 5, remote device 110 is shown displaying a second set of patient data. The patient data is derived from one or more medical devices 102, imaging device 102a, and/or audio device 102b.

Referring particularly to FIG. 3, in this embodiment, the first set of patient data includes a patient identifier 302, an oxygen saturation level 306, a pulse rate 308, respiration rate 310, blood pressure 312, temperature 314, ventilation 316, chart 318, alarm status 320, and general alarm status 321, threshold values, units of measurement, and placeholders where appropriate. The display parameters further include a pager 304 for navigating between the different sets of patient parameters.

In certain embodiments, patient identifier 302 may include a patient name and any appropriate patient notes, such as age, weight, height, and other appropriate information that a user might desire be readily accessible. Patient identifier 302 may also be a number or any other identifier to ensure patient privacy.

It will also be understood that alarm status 320 and/or general alarm status 321 may be indicated in any manner reasonable, such as a change in color or an audio indicator. Alarm status 320 and/or general alarm status 321 may be included for patients not currently in view, and, in certain embodiments, remote device 110 may be configured to page to an alarming patient automatically when alarm status 320 and/or general alarm status 321 for is triggered. According to one embodiment, the general alarm status 321 may provide an immediate indicator to the clinician as to which patient's data is in an alarming condition, while the alarm status 320 may signify which physiological parameter is in an alarm status. Other protocols for alerting the clinician to the patient and parameter causing the alarm may also be implemented without departing from the scope of the present disclosure.

Continuing with reference to FIG. 3, oxygen saturation level 306 is shown with values indicating upper and lower thresholds, 100 and 80, respectively, as well as a current value, 95 , and unit of measurement, percentage. Because the value of 95 is within the upper and lower thresholds, no alarm status 320 is shown. Similarly, pulse rate 308 and temperature 314 are shown with upper/lower thresholds, current values, and units of measurement without alarm status 320. In contrast, respiration rate 310 is shown with alarm status 320, because the value of 31 is not within the upper and lower thresholds of 30 and 10 respectively. In certain embodiments, thresholds may be set by medical devices 102, or by a clinician at the medical device 102 and transmitted to the remote device 110 as part of the patient data; in other embodiments, thresholds may be set by the user of remote device 110. It will be understood that certain physiological parameters may have a single threshold, such as an upper threshold or lower threshold, instead of a range.

In certain embodiments, remote device 110 may be configured to request a certain set of first display data, regardless of which display data are available, and display placeholders where no display parameters are provided. For example, blood pressure 312 and ventilation 316 are shown without threshold values or other data, indicating in certain embodiments that values have not been provided. In other embodiments, remote device 110 is configured to request and/or receive only those types of data for which values are available.

As shown in FIG. 3, chart 318, which relates to oxygen saturation levels, may be one of the data types displayed. Where appropriate, chart 318 may be scrollable and/or zoomable without interfering with the display of other data, such as pulse rate 308 or patient identifier 302. Chart 318 may include any data displayed in the form of a table, graph, or diagram and may include, for example, trend data, waveform data, and/or plethysmograph display data. The chart 318 can be generated for any physiological parameter of the patient and is selectable by the clinician to show longer term data sets of a physiological parameter. In certain embodiments, chart 318 may be automatically derived for a data type having an alarm status 320. That is, chart 318 may automatically show patient data relating to, for example, respiration rate 310 in the case of a patient experiencing a physiological condition causing the respiration monitor to alarm.

A clinician may scroll through chart 318 in a vertical or horizontal scroll mode. In certain other embodiments, a user may scroll through chart 318 and cause chart 318 to show patient data related to other physiological conditions for the patient shown, such as temperature 314, to obtain a history for those display parameters. Alternatively, a user may scroll through chart 318 related only to a selected type of patient data. For example, a user may click or select respiration rate 310 and scroll through a chart 318 related only to respiration rate 310.

As noted above, historical data may be viewed. This can be accomplished by selecting the data type and by altering the period for review from current to some longer term using, for example, a drop-down menu button or other appropriate selector. For example, where a current value is not available, such as the case of blood pressure 312 in FIG. 3, a user may view historical data related to blood pressure by selecting historical data related to blood pressure 312.

In some embodiments, a user may change the display to the previous or next patient by selecting the "PREV" or "NEXT" buttons 304, 305 on the display. The system may be configured such that a clinician can only have access to certain patients under their care via the remote device 110. For example, a clinician using remote device 110 may be limited to viewing patients located in the intensive care unit (ICU) of a hospital. In other embodiments, a clinician may be able to utilize the buttons 304, 305 to access different departments to which they have access to patients, for example, moving from patients in ICU to patients in Pediatrics. In certain embodiments, movement between patients may be limited or expanded as desired for a particular user, in any manner appropriate.

Figure 4:
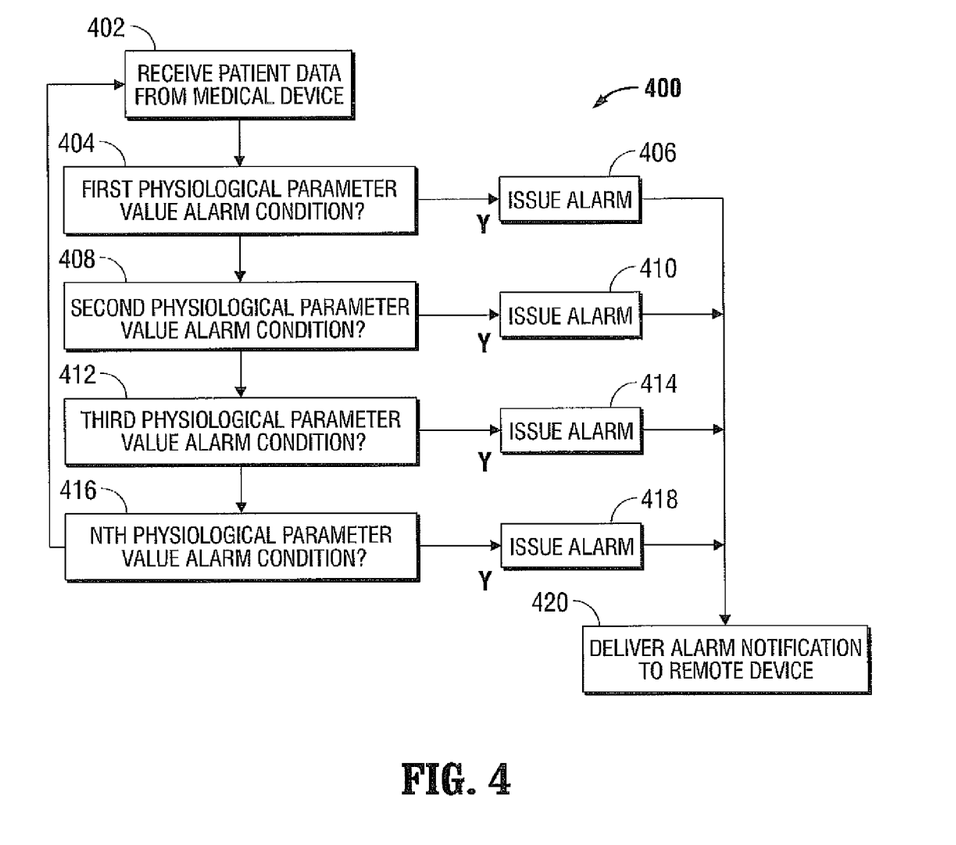
FIG. 4 is a flow chart depicting a basic alarm algorithm according to certain embodiments of the present disclosure.

Turning now to FIG. 4, a method for patient monitoring and determining an alarm condition is shown as method 400.

Beginning with step 402 of method 400, data collection server 104 of system 100 receives patient data from a first medical device 102. The data from the medical device 102 may be of a singular physiological parameter or multiple physiological parameters. Subsequent to receiving the patient data in step 402, at step 404, application server 106 accesses the data and determines if a first patient parameter is within an alarm condition. If yes, an alarm is issued at step 406. Regardless of the alarm in step 406, all the data will be analyzed by the application server 106 through the Nth physiological parameter at step 416. Each physiological parameter can trigger its own alarm at steps 410, 414, and 418. Following the analysis of the Nth physiological parameter, the method loops back to step 402 to receive a new data set and the analysis begins again. Alternatively, the medical device 102 could, along with the patient data, transmit to the data collection server 104, and therewith the application server 106, an indicator that the patient data is outside the alarm thresholds, therefore triggering the alarm at the application server 106. In step 420, application server 106 delivers an alarm notification to remote device 110 via the web sever 108. According to certain embodiments, the polling of, or the reporting by, the medical devices 102 of patient data to the data collection server 104 continues until all medical devices have reported and then the loop continues until the patient is no longer connected to a particular medical device 102. As will be appreciated, the data collected by the data collection server 104 may periodically transmit a discovery broadcast message to determine which medical devices 102 are connected to the patient and from which to gather patient data.

FIG. 3 depicts a remote device 110 with a first collection of patient data. Additionally, or alternatively, buttons 304, 305 may enable a clinician to move between different sets of patient data for the same patient, such as and without limitation, the second set of patient data discussed below with reference to FIG. 5.

Referring now to FIG. 5, additional patient data are displayed. The display of the remote device 110 also includes the patient identifier 302, and may include some of the data shown in FIG. 3, but in a summary form 330, for example without the acceptable ranges, or without certain less critical data. The additional data shown in FIG. 5 may include for example, image data in a display section 332, a volatility module 334, and a scroll bar 336, which are explained in greater detail below. Additionally, a user may rearrange, add, and/or remove any of the data displayed on remote device 110.

Continuing with reference to FIG. 5, image data appearing in display section 332 includes images and/or video obtained by imaging device 102a. Additionally, remote device 110 may further include a speaker (not shown) for delivering audio data, obtained by audio device 102b, corresponding to the video obtained by imaging device 120a and displayed in display section 332.

Accordingly, because the image or video data, and/or audio data are made available to a clinician, review of an alarm condition occurring with respect to one or more of the physiological parameters monitored by the medical devices 102 can be undertaken with all the advantages of the video data and audio data described above. That is, the video data and audio data help to put the alarm condition into context of the patient and their activities. Accordingly, an on-call physician can receive not only an indication that one of their patients is experiencing an alarm condition in one of their physiological parameters, but can also be able to see and hear the activity of that patient at or about the time of the alarm.

According to one aspect of the disclosure, the image data may be a series of still images taken at set intervals, for example every 10 seconds. As will be appreciated, image and video data, and audio data, can become voluminous and create significant burdens in storage, thus limiting the image data to single images every 10 seconds can greatly reduce the amount of data being stored. Alternatively, the image data may be video data that is constantly recorded and stored by the data server 104 along with the corresponding audio data.

Figure 6:
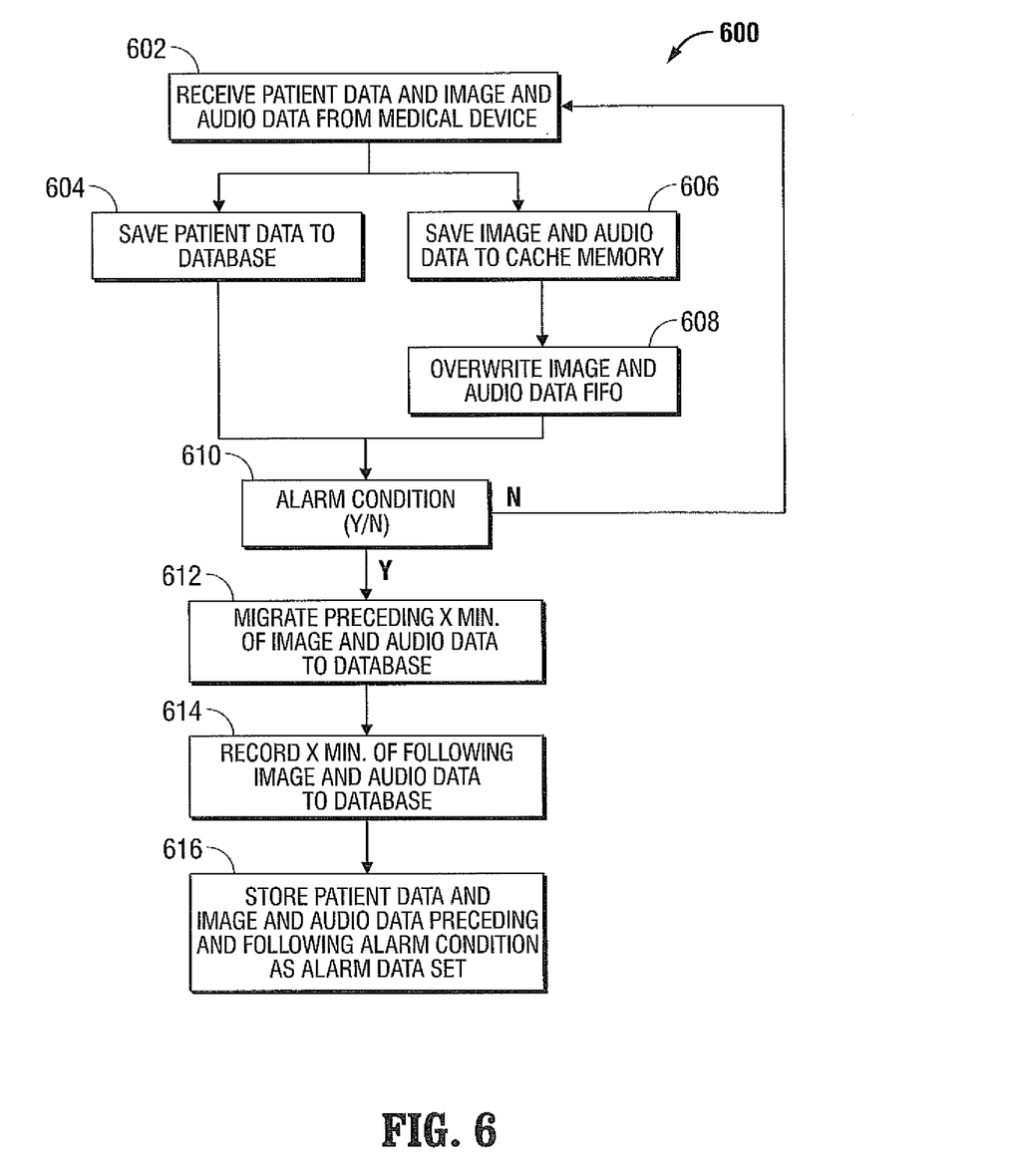
FIG. 6 is a flow chart depicting an image data recording protocol.

FIG. 6 depicts one exemplary protocol that may be employed such that the video data is being constantly overwritten in a cache memory capable of storing some set amount of video, for example five minutes. Although this exemplary protocol may be employed, it is also understood that database 104a may store all of the image data and audio data. At step 602 patient and image data are received from medical devices 102 and image device 102a, respectively. Although not shown in, audio data may also be received and processed, or otherwise stored, in the same manner as the image data described below. The patient data is stored in, for example, database 104a on data storage server 104 at step 604. The image data can also be stored on the data storage server 104, but in a more volatile condition at step 606. For example, only 5 minutes of video data might be stored on the data storage server 104 in a First-in-First-out (FIFO) cache memory. This leads to the most recent image data overwriting a portion of the previously received image data at step 608. If at any time an alarm condition is determined at step 610, then at least a portion of the image data stored in the cache at step 606 can be migrated into a longer term image memory at step 612. This longer term storage of image data may be accompanied by some duration of video following the alarm condition in step 614. This may be useful in depicting how the patient was treated following the alarm condition. Finally, the patient data along with the image data from steps 612 and 614 can be associated with one another in an alarm data set in step 616 that can be analyzed together either in real time or as part of the historical record of treatment.

In this way, only the video of image data, and/or audio data, relating to the alarm condition occurring at a particular time needs to be stored on the data server 104. This video or image data, and/or corresponding audio data, can be included in the patient data that is reviewable on the remote device 110 by the clinician in assessing the alarm condition. As will be apparent to one of skill in the art, the patient data being generated by the medical devices 102 at or around the time of the alarm condition may also be recorded such that the alarm data set includes the video/image data, audio data, the physiological parameters of the patient, and the subsequent actions of the clinicians (e.g., silencing the alarm, contacting attending physician, etc.) This alarm data set can include actions undertaken by a clinician from a remote device 110.

By storing these alarm data sets, including the video or image data, and audio data, historical information regarding a patient may be quickly and efficiently assessed and analyzed. To assist in this analysis, the present disclosure contemplates a visual representation of changes in the patient data, including instances of alarming conditions.

Volatility module 334, as shown in FIG. 5 is configured to represent changes in any of the patient parameters measured by medical devices 102, imaging unit 102*a*, and/or audio device 102*b*. As shown in FIG. 5, volatility module 334 takes the form of a bar graph, or chart similar to chart 318 of FIG. 3, which may be scrolled through, for example, by a user sliding their finger on the display surface. Changes in the patient parameters over a given period of time are captured and the corresponding bar in the volatility module 334 may represent a level of change in a patient parameter, or a group of patient parameters, associated with a particular time period. A user may select which patient parameter, or combination of patient parameters, to represent in the volatility module 334. For example and without limitation, a user may select that the volatility module 334 display volatility or changes with regard to the imaging parameters. With such a configuration, the bars in the volatility module 334 will represent the amount of movement detected in the video obtained by imaging device 102*a*. A significant movement by the patient may cause the bar corresponding to that particular period of time to be at a higher level that no movement by the patient. Generally, if there is an alarm condition in at least one parameter, the volatility module may indicate this with a large change in the volatility module 334, even if the absolute change in patient data were small. This is because the transition from a non-alarm state to an alarm state is of greater importance than a change in data that is still within the physiological parameter thresholds.

Additionally, a user may scroll over the bars in volatility module 334 to view the corresponding patient data, including the image data shown in display section 332, and the audio data received by audio device 102*b*, that existed at that given time scrolled to by the user. In use, this may assist a user or clinician to visualize activity of a patient over a given time displayed on the volatility module 334, and listen to audio data corresponding to that video data, and scroll to particular points that the clinician desires to view so that the clinician may make a determination of the severity of an alarm notification 320, or otherwise assess the alarming condition.

Scroll bar 336 is configured to enable a user to scroll through the images or video, displayed in the display section 332. A user may configure the remote device 110 such that scrolling through the scroll bar 336 causes a change in the data displayed. For example and without limitation, a user may select that the scroll bar 336 control only the display appearing in the display section 332, or alternatively a user may select that the scroll bar 336 controls the display of the volatility module 334, the display section 332, and other selected patient data. It is also envisioned that a user may manipulate the placement of the scroll bar 336, or otherwise rearrange any of the elements displayed on mobile device 110. Additionally, or alternatively, any of the elements appearing in the display section 332 of remote device 110 may be scrollable by a user swiping across the particular data displayed, as is well known in the area of user manipulatable graphical displays.

Another aspect of this method is that the application server 106 can analyze the image data and audio data and determine whether movement of the patient is detected. For example and without limitation, movement may be detected by comparing different time frames of the image parameters and determining if any changes are present. However, one skilled in the art would appreciate that movement may be detected by many other means including the use of separate components for detecting movement. According to the method of FIG. 7, the application server 106 determines that an alarm condition exists with respect to one of the physiological parameters of the patient data at step 702. Once the alarm condition is determined to exist, the application server 104 determines whether the physiological parameter causing the alarm condition is one that is movement volatile, step 704. For example, as described above, oximetry monitors for saturated oxygen levels are well known to be susceptible to inaccuracies due to patient movement. If the parameter causing the alarm is not one that is movement volatile, then the protocol ends and a notification of alarm is sent to the remote device 110 as discussed above, with respect to FIG. 4, step 706. If the physiological parameter is one that is movement volatile, the application server 106 can seek to determine if there was movement step 708. If no, at step 710 the alarm notification is forwarded to the remote device 110. If there is movement detected, at step 712 the application server can send notification of the movement to the remote device 110 along with a recommended action (e.g., silence alarm and ignore due to patient movement). At step 714, the clinician must either acknowledge and agree with the recommendation, at which point the recommended response is recorded in the data storage server 104, step 716, as having been agreed to by the clinician and the protocol ends. Alternatively, if the clinician disagrees, this too is stored at the data storage server 104 as are the clinician recommended responses at step 718 and the protocol ends.

Figure 7:
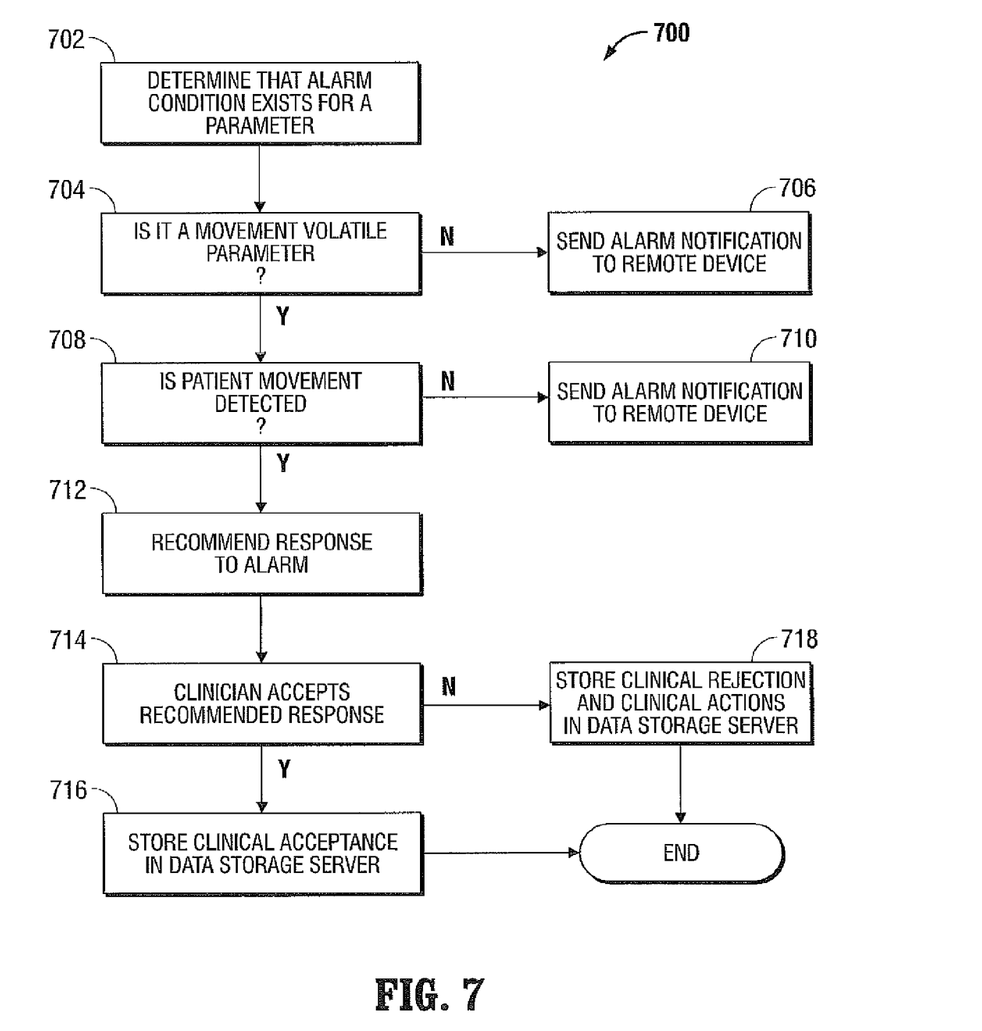
FIG. 7 is a flow diagram depicting a patient movement and response recommendation algorithm.

Continuing with reference now to FIG. 7, upon receiving the alarm notification and the image parameters or upon disagreeing with the recommended actions from the application server 106, as detailed above, a clinician may scroll through the video or series of images using scroll bar 336 or volatility module 334. With the image parameters and the corresponding audio data available to the clinician, a clinician may further assess the alarming condition and determine if physical movement by the patient may have been a cause or factor for a change in the patient parameter leading to the alarm. For example and without limitation, a patient may change from a sitting position to a standing position which may cause a brief and sudden change in one or several of the patient parameters. This change in one or several of the patient parameters may then cause the patient parameter to fall outside of the threshold, thus causing the delivery of an alarm notification 320. Providing the ability for the clinician to view image data in the display section 332, including the video and corresponding audio, of the patient during the time that the patient parameters fell outside of the threshold, enables the clinician to make the determination that the sudden change in the patient parameter was due to movement by the patient, and thus may be less alarming than if the sudden change in parameters took place without movement by the patient.

With respect to step 720, subsequent to delivering the image parameters for a clinician to review the alarm notification 320, patient parameters, and image parameters, data storage server 104 receives a clinician assessment of all of the information. For example, and without limitation, if the clinician determines that the alarm notification 320 (see FIG. 5) should be disregarded, due to the fact that the patient movement is what caused the alarm notification 320, the clinician may deliver the clinician assessment to the data collection server 104 to disregard the alarm notification 320. This clinician assessment is also stored in a database for future use. Future uses of the clinician assessment may include, without limitation, enabling a clinician to review the history of the patient, or historical data and patient parameters associated with the patient.

A further embodiment of the present disclosure is directed to a method of determining whether, despite no single patient datapoint results in an alarm condition, the combination of two or more datapoints warrants the triggering of an alarm condition. According to the method, application server 106 considers whether two or more of the patient parameters, though not by themselves representative of an alarm condition, when considered together do warrant the issuance of an alarm. For example, the application server 106 can analyze data from a blood pressure monitor and from a blood oximetry monitor. There may occur instances that despite neither one of these medical devices 102 outputting data that would otherwise result in an alarm condition, upon analyzing the two data set together their combination may reveal that an alarm is warranted. In determining whether to issue an alarm, the application server 106 can consider, not just the data from the medical devices 102 at a single point in time, but also the historical or trend data to determine whether an alarm is warranted to alert the necessary medical professionals.

A clinician may select the parameters that define the combined parameter and set the combination of values that result in a combined alarm. For example and without limitation, a user may desire the combined parameter to include a first and second patient parameters that are within 10% of either the maximum or minimum threshold values of their respective parameter. With such a parameter set for the combined threshold, the combined alarm notification will be delivered when the first parameter is within 10% of either the maximum or minimum threshold of the first patient parameter, and the second patient parameter is also within 10% of either the maximum or minimum threshold of the second patient parameter. As will be apparent, the combined parameter thresholds do not have to be for both the maximum and minimum, but can be selected to be for just one of these. Thus, for example, if the first parameter is pulse rate, and the second is blood oxygenation, only a combination of low oxygenation and low pulse rate might be selected for a combined threshold. Clinicians are able to select which combinations and subcombinations of patient data to employ for the combined alarms as described herein.

Figure 8:
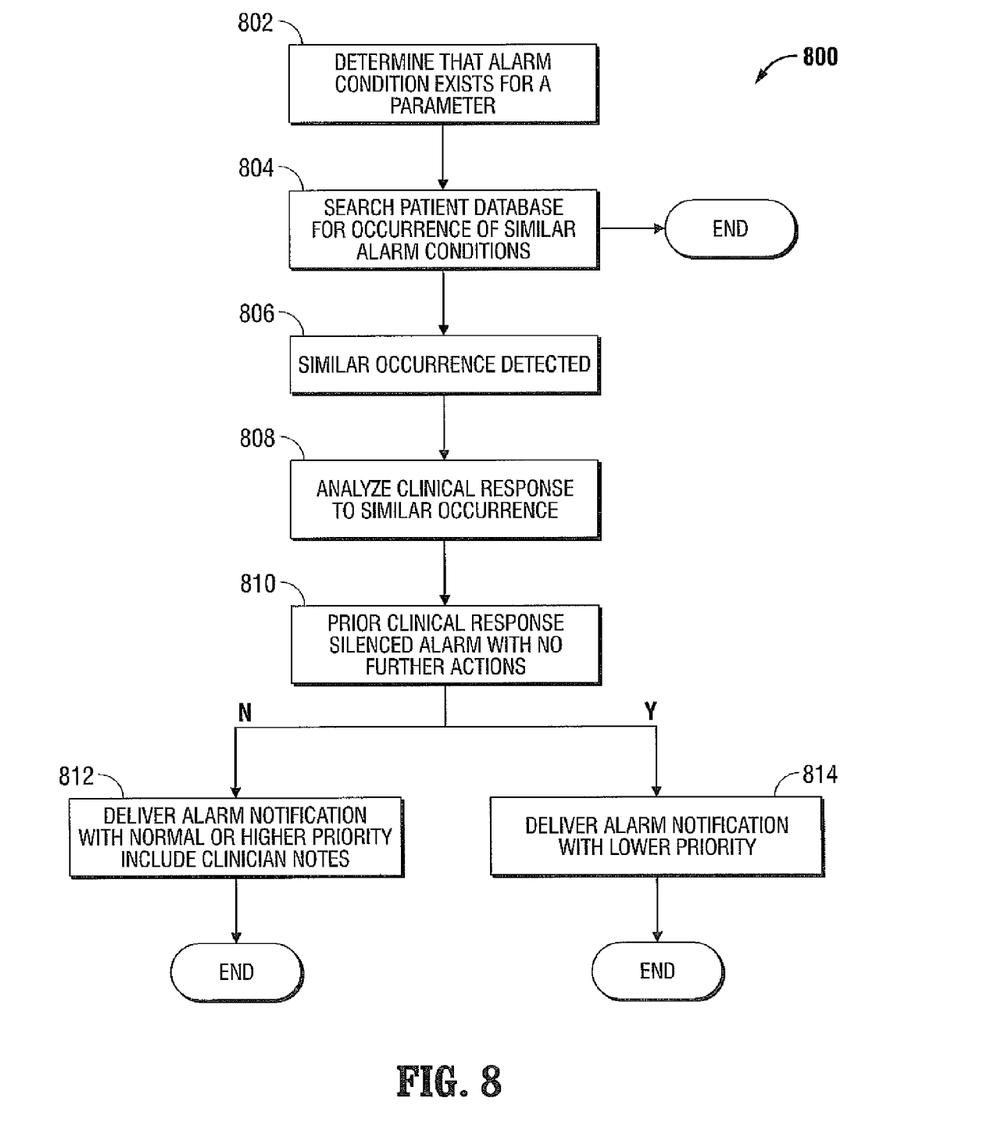
FIG. 8 is a flow diagram depicting an algorithm for analyzing an alarm condition for similar occurrences and making automated recommendations.

Turning to now FIG. 8, a method for patient monitoring and adaptive learning based on historical conditions is shown as method 800.

Method 800 begins at step 802 where application server 106 determines, or otherwise detects, an alarming condition. Upon determining, or otherwise detecting, an alarming condition at step 802, method 800 proceeds to step 804.

At step 804, application server 106 searches the database 104a for similar incidents. Similar incidents may include, without limitation, previous incidents where one, some, or all of the patient parameters were similar to the patient parameters that caused the alarming condition. If similar incidents are found in the database (YES in step 804), then method 800 proceeds to step 806. Alternatively, if related incidents are not found in the database (NO in step 804), then method 800 ends.

Following detection of similar incidents at step 806, application server 106 looks-up and analyzes the clinician assessment corresponding to the similar occurrence at step 808. At step 810 the application server determines whether the prior clinician assessment includes a silenced alarm (YES in step 810) and no further clinical steps, then method 800 proceeds to step 814. Alternatively, if the prior clinician assessment does include additional steps by the clinician (NO in step 810), then method 800 proceeds to step 812. In step 814, application server 106 delivers the alarm notification with a lower priority. Delivering the alarm notification with a lower priority may include, for example and without limitation, delivering the alarm notification in a different color, a lower volume, with a statement regarding automatic analysis for clinician agreement, or even not delivering the alarm notification at all. In step 812, however, where the prior clinician assessment did include further clinical steps (NO in step 810), application server 106 delivers the alarm notification either as it usually would, or with a higher priority. Step 812 may further include delivering previous clinician notes that are associated with the prior clinician assessment and actions. Delivering the alarm notification with a higher priority may include, for example and without limitation, changing the color of the notification, or increasing the sound of the alarm notification. Subsequent to completing either of steps 812 or 814, method 800 ends.

Certain embodiments of the present disclosure comprise logic for patient monitoring, such as mobile patient monitor 214 of FIG. 2, and may be embodied in at least one tangible, computer-readable medium. For example, when the logic is executed, it may be operable to receive one or more types of patient data from at least one machine, transform the patient data for display and update the display in response to receiving updated patient data. The display may comprise one or more of a patient identifier, a patient status, one or more physiological parameters being monitored by the medical devices, image data, audible data, and an alarm condition In certain embodiments, the logic for patient monitoring may be embodied in more than one tangible, computer-readable medium. For example, portions of the logic for patient monitoring may be embodied in one or more of medical device 102, data collection server 104, application server 106, web server 108, and remote device 110 of system 100 in any manner.

Although the present disclosure describes certain embodiments, various alterations and permutations of the embodiments will be apparent to those skilled in the art. Accordingly, the above description of the embodiments does not constrain this disclosure. Other changes, substitutions, and alterations are possible without departing from the spirit and scope of this disclosure, as defined by the following claims.

What is claimed is:

1. A method comprising:
   receiving data indicative of at least one physiological parameter of a patient;
   receiving image data of the patient;
   analyzing and processing, by an application server, the image data of the patient to determine if the patient has moved;

determining that a value of the at least one physiological parameters signifies an alarm condition of the patient;

generating an alarm data set including image or audio data of the patient and the value of at least one physiological parameter when determined that the value of the at least one physiological parameter signifies an alarm condition of the patient; and transmitting a notification of the alarm condition including the alarm data set to a clinician.

2. The method of claim 1, wherein the image data includes video data of a patient before and after the occurrence of the alarming condition.

3. The method of claim 1, further comprising determining whether the at least one physiological parameter signifying an alarm condition is a movement volatile parameter.

4. The method of claim 3, further comprising determining whether the image data indicates movement of the patient at the occurrence of the alarm condition.

5. The method of claim 4, further comprising generating an automatic recommendation for responding to the transmitted notification of the alarm condition when determined that the at least one physiological parameter is movement volatile and that the patient moved.

6. The method of claim 1, further comprising transmitting a notification of the alarm condition to a remote device.

7. The method of claim 6, further comprising receiving input data that addresses the notification from the remote device.

8. The method of claim 6, further comprising displaying the image data of the alarm data set on the remote device.

9. The method of claim 6, further comprising receiving a request for additional data related to the notification.

10. The method of claim 1, wherein the at least one physiological parameter of the patient whose value is determined to signify an alarm condition is comprised of two physiological parameters which individually signify no alarm condition.

11. The method of claim 1, further comprising analyzing image data of the alarm data set to determine whether movement of the patient was a factor in causing the at least one physiological parameter to signify an alarm condition.

12. A remote device for analyzing patient data comprising:
a transmit/receiver connecting the remote device to a data source;
an application server processing data received from or transmitted to the data source, the data including patient data from one or more medical devices monitoring at least one physiological parameter of a patient and image data of the patient; and
a display on which visual representations of the at least one physiological parameter can be viewed, the display including the image data or audio data of the patient and a volatility module, wherein the application server is configured to analyze the image data to determine if the patient has moved and wherein the volatility module is configured to identify instances of historical patient data where a value of one or more patient data points experienced a medically significant change.

13. The remote device of claim 12, further comprising a scroll bar allowing a clinician to scroll from one indicator to the next on the volatility module.

14. The remote device of claim 12, wherein the display depicts a historical graph of at least one physiological parameter among the patient data.

15. The remote device of claim 12, wherein user inputs to the remote device are transmitted to the data source and stored as part of the patient data.

16. The remote device of claim 12, wherein a notification alarm condition in the patient received from the data source can be analyzed and responded to by a clinician.

17. A non-transitory computer readable recording medium, storing a computer program, which, when executed by a computer, causes a computer to perform a method comprising:
receiving at an application server data indicative of at least one physiological parameter of a patient and image data of the patient;
determining by the application server that a value of the at least one physiological parameters signifies an alarm condition in the patient;
generating an alarm data set including image or audio data of the patient and the value of the at least one physiological parameter;
transmitting an alarm notification of the alarm condition including the alarm data set to a web server for publication on a web-page, the web-page being accessible by one or more remote devices for clinical analysis of the alarm data set.

18. The non-transitory computer readable recording medium of claim 17, wherein data input from a remote device regarding the alarm notification is received by the application server and included as part of the alarm data set.

19. The non-transitory computer readable recording medium of claim 17, wherein the image data includes video data from before and after the determination of an alarm condition.

20. The non-transitory computer readable recording medium of claim 17, wherein the alarm data set includes an indication that movement by the patient is a factor in causing physiological parameters to signify an alarm condition.

* * * * *